(12) United States Patent
Lawrence

(10) Patent No.: US 7,992,748 B2
(45) Date of Patent: Aug. 9, 2011

(54) EARPLUG DISPENSER

(75) Inventor: Michael Paul Lawrence, Johnston, RI (US)

(73) Assignee: North Safety Products, Inc., Cranston, RI (US)

( * ) Notice: Subject to any disclaimer, the term of this patent is extended or adjusted under 35 U.S.C. 154(b) by 784 days.

(21) Appl. No.: 11/601,398

(22) Filed: Nov. 17, 2006

(65) Prior Publication Data

US 2008/0116219 A1    May 22, 2008

(51) Int. Cl.
*G07F 11/16* (2006.01)

(52) U.S. Cl. ................... 221/203; 221/256; 221/277

(58) Field of Classification Search ............... 221/203, 221/186, 265, 258
See application file for complete search history.

(56) References Cited

U.S. PATENT DOCUMENTS

| | | | | |
|---|---|---|---|---|
| 2,535,928 A * | 12/1950 | Ives | ............ | 99/561 |
| 2,630,245 A * | 3/1953 | Maier | ............ | 221/264 |
| 2,772,811 A * | 12/1956 | Schaef | ............ | 221/155 |
| 2,904,230 A * | 9/1959 | Worth | ............ | 222/452 |
| 3,730,387 A * | 5/1973 | McConnell et al. | ............ | 221/265 |
| 3,811,599 A * | 5/1974 | O'Connor | ............ | 221/265 |
| 3,885,703 A * | 5/1975 | Neavin | ............ | 221/202 |
| 4,782,981 A * | 11/1988 | Schuster | ............ | 221/265 |
| 5,014,877 A * | 5/1991 | Roos | ............ | 221/265 |
| 5,280,845 A * | 1/1994 | Leight | ............ | 221/2 |
| 5,285,925 A | 2/1994 | Leight | | |
| 5,316,517 A * | 5/1994 | Chiba et al. | ............ | 453/57 |
| 5,322,185 A | 6/1994 | Leight | | |
| 5,372,278 A | 12/1994 | Leight | | |
| 5,695,395 A * | 12/1997 | Ota et al. | ............ | 453/57 |
| 5,954,229 A * | 9/1999 | Scholey et al. | ............ | 221/186 |
| D424,340 S | 5/2000 | Fleming | | |
| 6,241,120 B1 * | 6/2001 | Scholey et al. | ............ | 221/186 |
| 6,283,339 B1 * | 9/2001 | Morrow | ............ | 222/452 |
| 6,299,019 B1 * | 10/2001 | Leight | ............ | 221/186 |
| 6,604,653 B2 * | 8/2003 | Millar | ............ | 221/203 |
| 6,991,131 B2 | 1/2006 | Maser | | |
| 2006/0006189 A1 * | 1/2006 | Curtolo et al. | ............ | 221/178 |

* cited by examiner

*Primary Examiner* — Gene Crawford
*Assistant Examiner* — Kelvin L Randall, Jr.
(74) *Attorney, Agent, or Firm* — Wood, Phillips, Katz, Clark & Mortimer

(57) ABSTRACT

An earplug dispenser (10) includes a container (12), a cover (14), and a rotatable member (16). The container (12) is adapted to hold a quantity of earplugs (18) to be dispensed, and has a downwardly opening mouth (20). The cover (14) is attached to the container (12) to close the downwardly opening mouth (20). The rotatable member (16) is carried in the cover (14) for rotation about a vertical axis (22). The cover (14) has a base (24), a dispensing port (26) extending through the base (24), and a facing cylindrical surface (28A) extending up from the base (24) and centered on the vertical axis (22). The rotatable member (16) has a plurality of conduits (29) extending vertically through the rotatable member (16), with each conduit (29) adapted to receive an earplug (18) from the container (12) and align one at a time with the dispensing port (26) to allow an earplug (18) carried in the conduit (29) to be dispensed downwardly through the dispensing port (26). The rotatable member (16) has an outer peripheral surface 34 at least partially surrounded by the cylindrical surface (28A) and accessible through an aperture (30) formed in the cover (14) for manual rotation of the rotatable member (16). The peripheral and cylindrical surfaces (34,28A) are sized relative to each other to prevent earplugs 18 from jamming therebetween during rotation of the rotatable member (16).

11 Claims, 4 Drawing Sheets

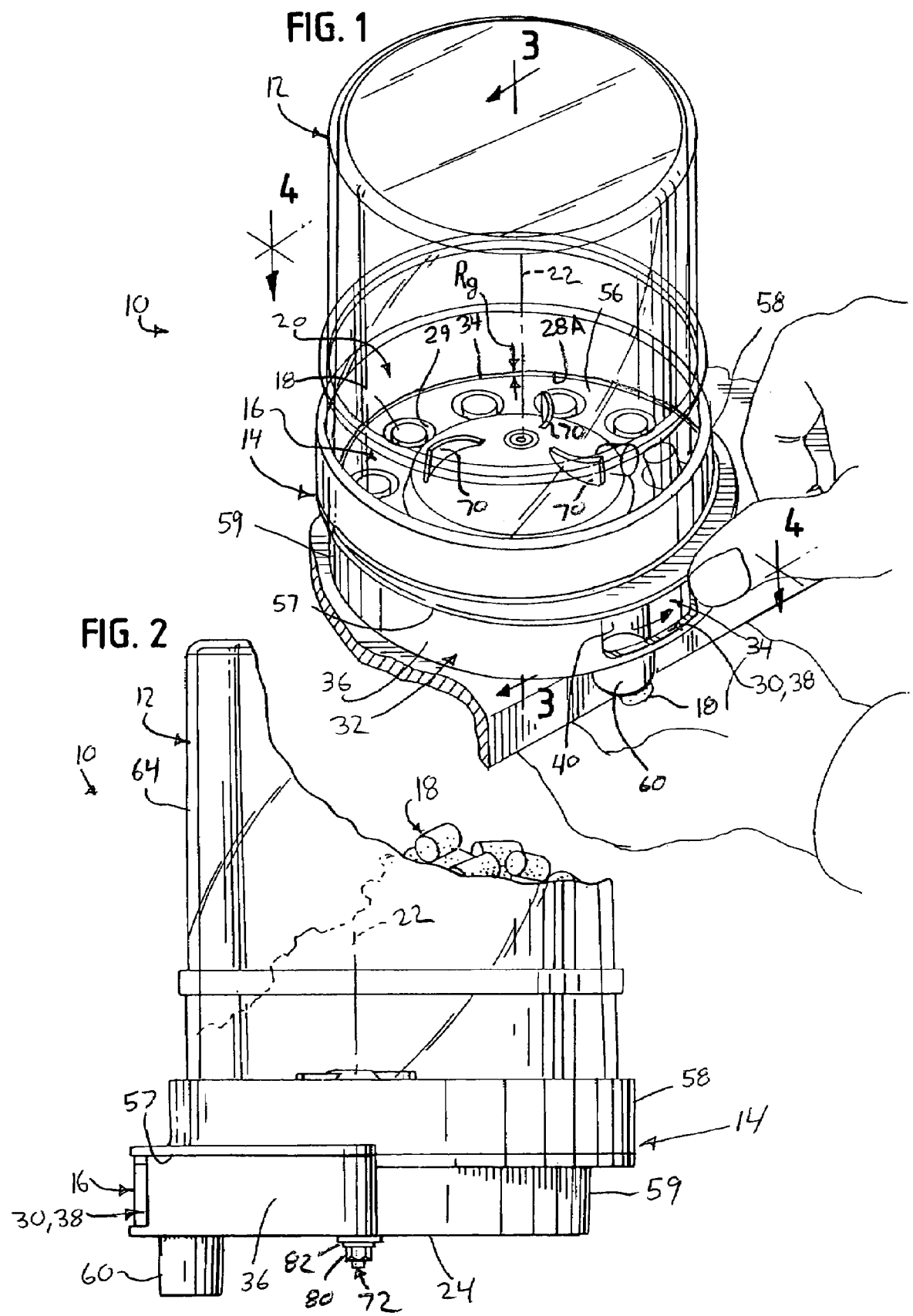

US 7,992,748 B2

EARPLUG DISPENSER

CROSS-REFERENCE TO RELATED APPLICATIONS

Not Applicable.

FEDERALLY SPONSORED RESEARCH OR DEVELOPMENT

Not Applicable.

MICROFICHE/COPYRIGHT REFERENCE

Not Applicable.

FIELD OF THE INVENTION

This invention relates to safety equipment, and more specifically to dispensers for storing and dispensing earplugs.

BACKGROUND OF THE INVENTION

There are many known forms of earplug dispensers wherein a rotatable member can be manually rotated to dispense one earplug at a time from a container. Examples of such earplug dispensers are shown in U.S. Pat. Nos. 5,280,845; 5,285,925; 5,322,185; 5,372,278; 5,954,229; 6,241,120; and 6,299,019. While the known earplug dispensers may work well for their intended purpose, there is always room for improvement in such devices. For example, there is a continuing desire for simplification, cost reduction, and/or reliability.

SUMMARY OF THE INVENTION

In accordance with one feature of the invention, an earplug dispenser includes a container adapted to hold a quantity of earplugs to be dispensed, the container having a downwardly opening mouth; a cover attached to the container to close the downwardly opening mouth; and a rotatable member carried in the cover for rotation about a vertical axis. The cover has a base, a dispensing port extending through the base, and an inwardly facing cylindrical surface extending up from the base and centered on a vertical axis, the cylindrical surface having an aperture formed therethrough to an exterior of the cover. The rotatable member has a plurality of conduits extending vertically through the rotatable member, each conduit adapted to receive an earplug from the container. The conduits are arranged in an annular array about the vertical axis to align one at a time with the dispensing port to allow an earplug carried in the conduit to be dispensed downwardly through the dispensing port. The rotatable member further has an outer peripheral surface surrounded by the cylindrical surface of the cover and accessible through the aperture in the cover for manual rotation of the rotatable member. The peripheral and cylindrical surfaces are sized relative to each other to prevent earplugs from jamming between the surfaces.

In one feature, the cover further includes a cylindrical bearing surface extending from the base and centered on the vertical axis, and the rotatable member further includes a cylindrical journal surface engaged with the cylindrical bearing surface to guide the rotatable member for rotation about the vertical axis. As a further feature, the cylindrical bearing surface is defined by an annular slot in the base.

As one feature, the cover further includes an outwardly facing cylindrical periphery opposite the inwardly facing cylindrical surface, and the aperture defines a circumferentially extending window to expose the peripheral surface of the rotatable member.

According to one feature, the rotatable member further includes an upwardly facing annular surface, and the cover further includes a downwardly facing guide surface spaced from the base and positioned to engage the annular surface to limit upward movement of the rotatable member.

In one feature, the rotatable member is supported on the base.

In accordance with one feature, the dispensing port includes a circular opening in the base.

As one feature, the dispensing port includes a cylindrical wall extending downward from the base.

According to one feature, the conduits have a cylindrical shape.

In one feature, the outer peripheral surface has a cylindrical shape that is interrupted by an array of angularly spaced indents.

As one feature, the container includes a cylindrical wall extending upwardly from the mouth and offset from the vertical axis.

Other advantages, features, and objects of the invention will become apparent after a detailed reading of the entire specification, including the appended claims and drawings.

BRIEF DESCRIPTION OF THE DRAWINGS

FIG. 1 is a perspective view from above of an earplug dispenser embodying the present invention as supported on a table and being manipulated by a user's hands;

FIG. 2 is a side view of the dispenser of FIG. 1;

DETAILED DESCRIPTION OF THE PREFERRED EMBODIMENT

Figure 3:
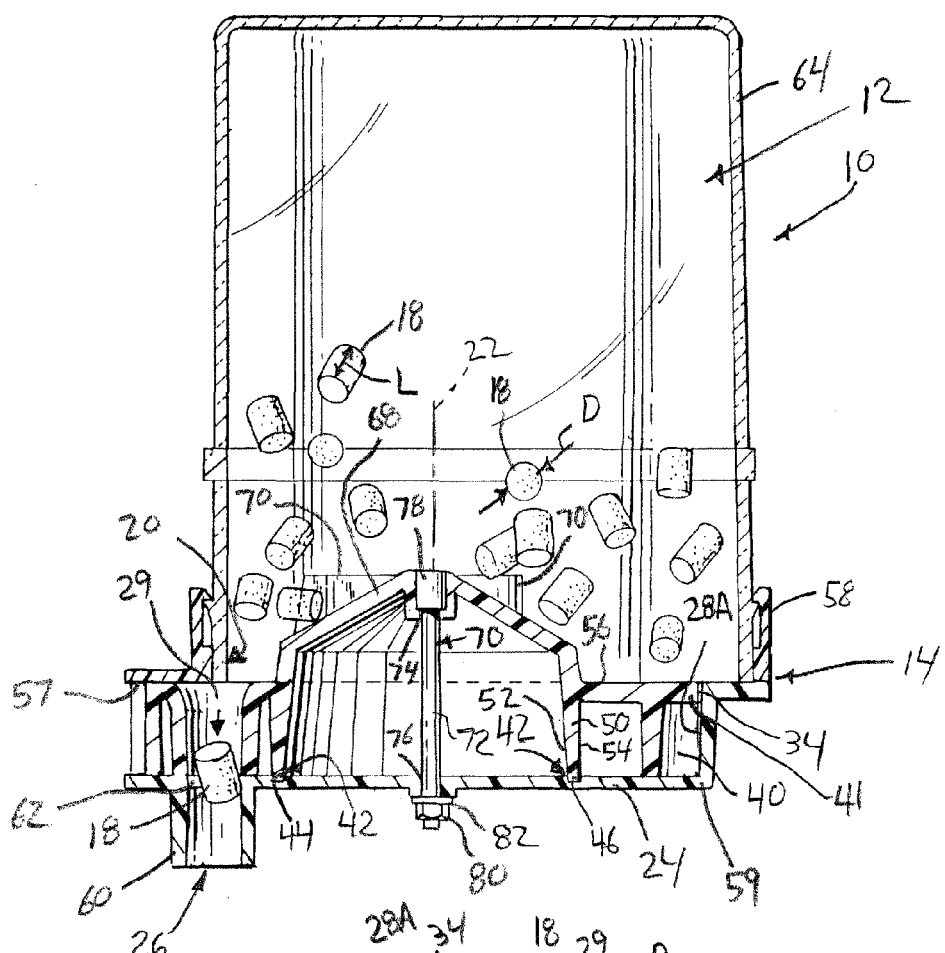
FIG. 3 is a section view taken generally along line 3-3 in FIG. 1.

As best seen in FIGS. 1-3, an earplug dispenser 10 includes a container 12, a cover 14, and a rotatable member 16. The container 12 is adapted to hold a quantity of earplugs 18 (for purposes of illustration, only a few of the earplugs are shown in the Figs.) to be dispensed, and has a downwardly opening mouth 20. The cover 14 is attached to the container 12 to close the downwardly opening mouth 20. The rotatable member 16 is carried in the cover 14 for rotation about a vertical axis 22.

As best seen in FIG. 3, the cover 14 has a base 24, a dispensing port 26 extending through the base 24, and an inwardly facing surface 28 extending up from the base 24. In the illustrated embodiment, the inwardly facing surface 28 is divided into first and second cylindrical surfaces 28A and 28B, both centered on the vertical axis 22. The cylindrical surface 28A underlies the container 12, while the cylindrical surface 28B does not underlie the container 12.

Figure 4:
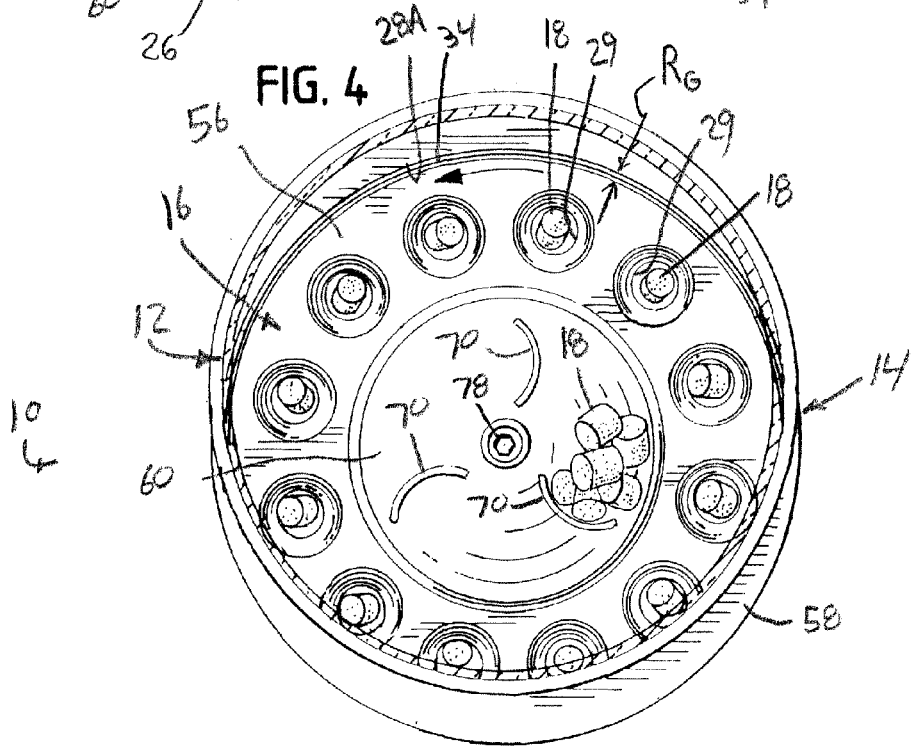
FIG. 4 is a section view taken from line 4-4 in FIG. 1.
Figure 5:
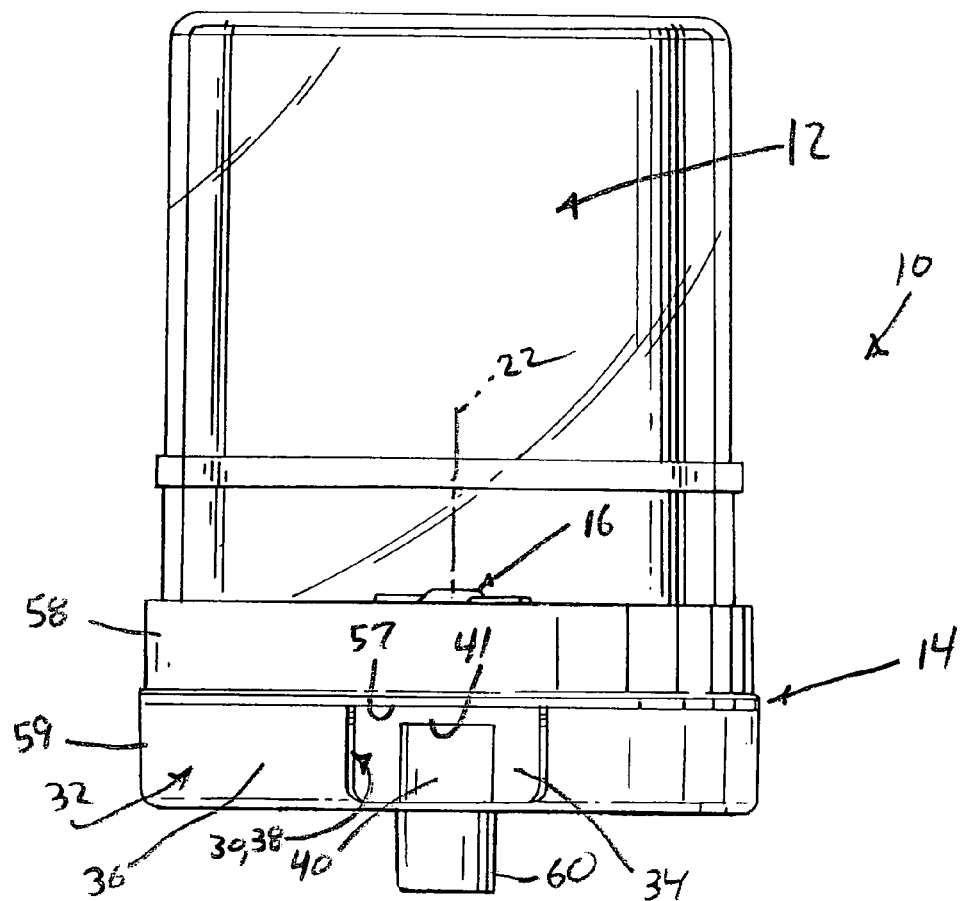
FIG. 5 is a front view of the dispenser of FIG. 1.
Figure 6:
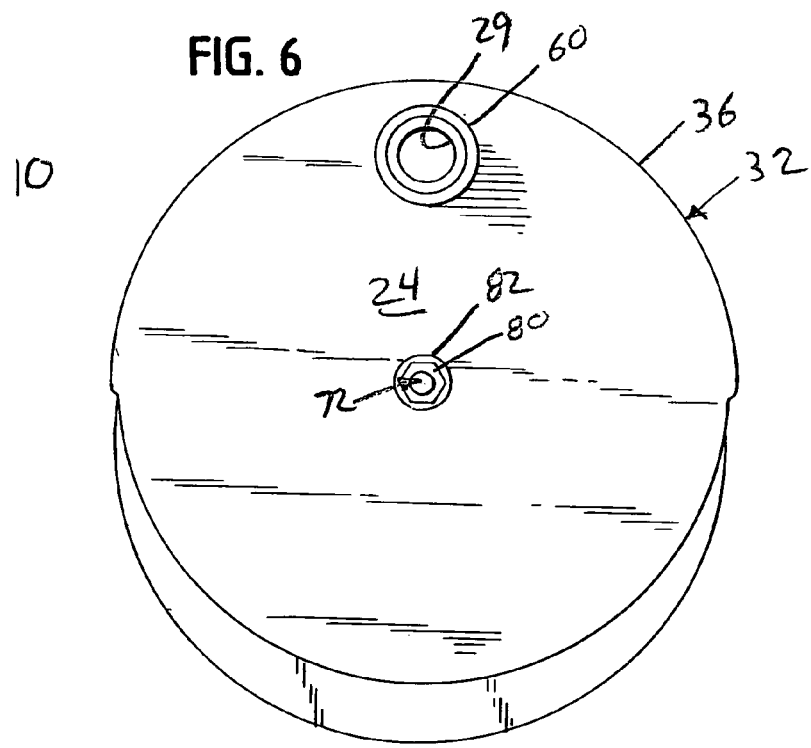
FIG. 6 is a bottom view of the dispenser of FIG. 1.

As best seen in FIG. 4, the rotatable member 16 has a plurality of conduits 29 extending vertically through the rotatable member 16. Each conduit 29 is adapted to receive an earplug 18 from the container 12. In this regard, it is preferred that each of the conduits 29 have a cylindrical shape, however, depending on the application other shapes may be desirable. The conduits 29 are spaced in an annular array about the vertical axis 22 to align one at a time with the dispensing port 26 to allow an earplug 18 carried in the conduit 29 to be dispensed downwardly through the dispensing port 26, as seen in FIG. 3. The conduits 29 are preferably equally spaced around the annular array, but unequal spacing may be used if desired.

The cylindrical surface 28B of the cover 14 has an aperture 30 formed therethrough to an exterior 32 of the cover 18. The rotatable member 16 has an outer peripheral surface 34 surrounded by the surface 28 and accessible through the aperture 30 for manual rotation of the rotatable member 16, as best seen in FIG. 1. The peripheral and cylindrical surfaces 34 and 28A are sized relative to each other to prevent earplugs 18 from jamming between the surfaces 34 and 28A during rotation of the rotatable member 16. This is desirable because the cylindrical surface 28A underlies the container and is therefore exposed to the earplugs 18 contained therein. In this regard, the surfaces 34 and 28A are sized so that a radial gap Rg exists between the surfaces 34 and 28A to allow rotation of the rotatable member 16, with the size of the gap Rg preferably not exceeding the smallest un-deformed diametric D dimension or length L dimension of the earplugs 18. While the cylindrical surface 28B does not underlie the container 12, and is therefore not exposed to the earplugs 18 contained therein, it may still be desirable for the surfaces 34 and 28B to be sized similar to the relative sizing of surfaces 34 and 28A.

Preferably, the exterior 32 is defined by an outwardly facing cylindrical surface 36 opposite the inwardly facing cylindrical surface 28, and the aperture 30 defines a circumferentially extending window 38 to expose the peripheral surface 34 of the rotatable member 16. In this regard, it is preferred that the circumferential length $L_c$ of the window 38, best seen in FIG. 7, be of a length that corresponds to the circumferential spacing from one conduit 29 to the next so that the rotatable member 16 will move from one conduit 29 to the next conduit 29 by manual engagement of the rotatable member 16 at one circumferential end of the window 38 and then moving the rotatable member 16 to the other circumferential end of the window 38. Preferably, although not required, the peripheral surface 34 has a generally cylindrical shape that is periodically interrupted by angularly spaced indents 40 that can be engaged by a user's finger(s) during manual rotation of the rotatable member 16, as seen in FIG. 1. In this regard, it should be appreciated that there are many possible forms for the indents 40, including simple serrations, and that the particular form shown is for purposed of illustration. It should also be appreciated that, depending on the size of the indents 40, the indents 40 do not extend over the entire vertical extent of the peripheral surface 34 so that they leave an uninterrupted portion or lip 41 of the surface 34 at the top of each indent 40 that maintains the radial gap $R_g$, as best seen in FIG. 3

Figure 7:
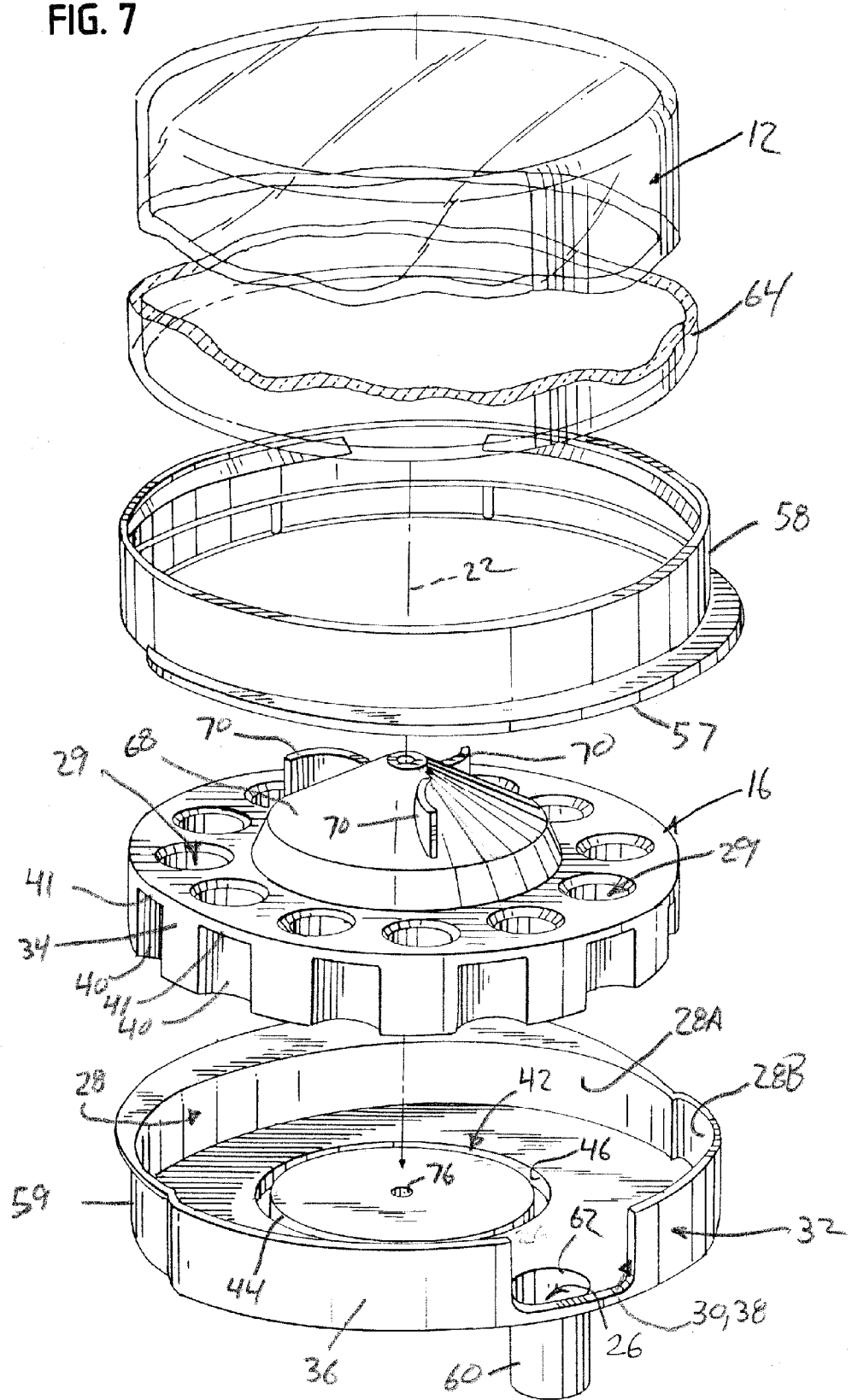
FIG. 7 is an exploded, perspective view of the dispenser of FIG. 1.

Preferably, as best seen in FIGS. 3 and 7, the cover 14 also includes an annular slot 42 in the base 24 defining a pair of cylindrical bearing surface 44 and 46 centered on the vertical axis 22. The rotatable member 16 further includes a cylindrical flange 50 defining a pair of cylindrical journal surfaces 52 and 54 that engage with the cylindrical bearing surfaces 44 and 46, respectively, to guide the rotatable member 16 for rotation about the vertical axis 22.

The rotatable member 16 also preferably includes an upwardly facing annular surface 56, and the cover 14 includes a downwardly facing surface 57 overlying the cylindrical surface 28B and the annular surface 56 adjacent thereto. In this regard, in the illustrated embodiment, the cover 14 is actually a two-piece construction, with a first piece 58 defining the surface 56 and a cylindrical rim for connection to the container 12, and the second part 59 defining the remaining features of the cover 14.

As shown in the illustrated embodiment, the dispensing port 26 includes a cylindrical wall 60 extending downward from a circular opening 62 in the base 24. It should be appreciated, that there are many possible configurations for the dispensing port 26, with the particular configuration depending upon the particular requirements of each application.

In the illustrated embodiment, the container 12 includes a cylindrical wall 64 that extends upwardly from the mouth 20 and is offset from the vertical axis 22. It is also preferred that the wall 64 be transparent. It should be appreciated that while the cylindrical wall 64 is shown, any suitable shape may be used for the container 12, including a rectangular box shape.

As best seen in FIG. 3, it is also preferred that the rotatable member include a cone shaped central portion 68 with at least one vertically extending push vane 70 to assist in moving the earplugs 18 towards the conduits 29 during rotation of the rotatable member 16. Preferably, there are three push vanes 70, with each of the push vanes 70 being curved, as best seen in FIG. 1. It should be appreciated that other shapes for the central portion 68 and the vanes 70 may be desirable depending upon the specific requirements of each application.

As best seen in FIG. 3, the dispenser 10 preferably includes a suitable fastener, such as a threaded fastener 72, extends along the vertical axis 22 through openings 74 and 76 provided in the rotatable member 16 and the cover 14, respectively, to limit upward movement of the rotatable member 16 relative to the base 24 of the cover 14. In the illustrated embodiment, the threaded fastener 72 includes a head 78 engaged with the rotatable member 16 and a nut 80 engaged with an opposite end of the fastener 72, with a washer 82 sandwiched between the threaded nut 80 and the base 24. It will appreciated by those skilled in the art that there are many possible variations for this structure.

It should be understood that each of the cylindrical shapes, surfaces, or walls described herein may have a slight taper so as to allow for manufacturing of the corresponding component using a suitable molding technique, which may require the taper to allow for the release of the mold dies or forms. Accordingly, as used herein, the term cylindrical includes shapes, surfaces, and walls that include such tapers.

The invention claimed is:

1. An earplug dispenser comprising:
 a container adapted to hold a quantity of earplugs to be dispensed, the container having a downwardly opening mouth;
 a cover attached to the container to close the downwardly opening mouth, the cover having:
  a base,
  a dispensing port extending through the base, and
  an inwardly facing surface extending up from the base, at least part of the inwardly facing surface being a cylindrical surface underlying the container and centered on a vertical axis, the inwardly facing surface having an aperture formed therethrough to an exterior of the cover;
 a rotatable member carried in the cover for rotation about the vertical axis, the rotatable member having a plurality of conduits extending vertically through the rotatable member, each conduit adapted to receive an earplug from the container, the conduits arranged in an annular array about the vertical axis to align one at a time with the dispensing port to allow an earplug carried in the conduit to be dispensed downwardly through the dispensing port, the rotatable member having an outer peripheral surface surrounded by said inwardly facing surface of the cover and accessible through said aperture in the cover for manual rotation of the rotatable member, the peripheral and cylindrical surfaces sized relative to each other to prevent earplugs from jamming between said surfaces;

wherein:

the rotatable member further comprises an upwardly facing annular surface; and the cover is a two-piece construction, with one of the pieces defining the inwardly facing surface, and the other piece defining a downwardly facing surface overlying part of the rotatable member.

2. An earplug dispenser comprising:

a container adapted to hold a quantity of earplugs to be dispensed, the container having a downwardly opening mouth;

a cover attached to the container to close the downwardly opening mouth, the cover having:
   a base,
   a dispensing port extending through the base, and
   an inwardly facing surface extending up from the base, at least part of the inwardly facing surface being a cylindrical surface underlying the container and centered on a vertical axis, the inwardly facing surface having an aperture formed therethrough to an exterior of the cover;

a rotatable member carried in the cover for rotation about the vertical axis, the rotatable member having a plurality of conduits extending vertically through the rotatable member, each conduit adapted to receive an earplug from the container, the conduits arranged in an annular array about the vertical axis to align one at a time with the dispensing port to allow an earplug carried in the conduit to be dispensed downwardly through the dispensing port, the rotatable member having an outer peripheral surface surrounded by said inwardly facing surface of the cover and accessible through said aperture in the cover for manual rotation of the rotatable member, the peripheral and cylindrical surfaces sized relative to each other to prevent earplugs from jamming between said surfaces; and wherein another part of the inwardly facing surface does not underlie the container; and the cover includes a surface that overlies the another part of the inwardly facing surface and part of the rotatable member.

3. The earplug dispenser of claim 2 wherein:

the cover further comprises a cylindrical bearing surface extending from the base and centered on the vertical axis; and the rotatable member comprises a cylindrical journal surface engaged with the cylindrical bearing surface to guide the rotatable member for rotation about the vertical axis.

4. The earplug dispenser of claim 3 wherein the cylindrical bearing surface is defined by an annular slot in the base.

5. The earplug dispenser of claim 2 wherein the cover further comprises an outwardly facing cylindrical surface opposite the inwardly facing surface, and the aperture defines a circumferentially extending window in the outwardly facing cylindrical surface to expose the peripheral surface of the rotatable member.

6. The earplug dispenser of claim 2 wherein the rotatable member is supported on said base.

7. The earplug dispenser of claim 2 wherein the dispensing port comprises a circular opening in the base.

8. The earplug dispenser of claim 2 wherein the dispensing port comprises a cylindrical wall extending downward from the base.

9. The earplug dispenser of claim 2 wherein the conduits have a cylindrical shape.

10. The earplug dispenser of claim 2 wherein the outer peripheral surface has a cylindrical shape that is interrupted by an array of angularly spaced indents.

11. The earplug dispenser of claim 2 further comprising a fastener extending along the vertical axis and engaged with the rotatable member in the base to limit upward movement of the rotatable member relative to the base.

* * * * *